US 11,890,690 B2

(12) United States Patent
Govari et al.

(10) Patent No.: US 11,890,690 B2
(45) Date of Patent: Feb. 6, 2024

(54) PREPARATION OF MICRO-ELECTRODES

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US); Joseph Thomas Keyes, Glendora, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 1212 days.

(21) Appl. No.: 16/255,729

(22) Filed: Jan. 23, 2019

(65) Prior Publication Data

US 2019/0336021 A1 Nov. 7, 2019

Related U.S. Application Data

(62) Division of application No. 14/886,761, filed on Oct. 19, 2015, now Pat. No. 10,213,856.

(51) Int. Cl.
*A61B 18/14* (2006.01)
*B23H 1/04* (2006.01)
(Continued)

(52) U.S. Cl.
CPC ............ *B23H 1/04* (2013.01); *A61B 5/25* (2021.01); *A61B 5/283* (2021.01); *A61B 5/291* (2021.01);
(Continued)

(58) Field of Classification Search
CPC ......... A61B 5/339; A61B 5/291; A61B 5/283; A61B 5/25; A61B 5/6852; A61B 18/082;
(Continued)

(56) References Cited

U.S. PATENT DOCUMENTS

| 4,566,467 A | 1/1986 | Dehaan |
| 4,649,937 A | 3/1987 | Dehaan et al. |

(Continued)

FOREIGN PATENT DOCUMENTS

| CN | 103584853 A | 2/2014 |
| JP | H08-503381 | 4/1996 |

(Continued)

OTHER PUBLICATIONS

European Search Report dated Mar. 27, 2017 from corresponding European Patent Application No. 16194402.0.
(Continued)

*Primary Examiner* — Adam Z Minchella
(74) *Attorney, Agent, or Firm* — Lewis Roca Rothgerber Christie LLP (57) ABSTRACT

A method, consisting of providing a metal wire having a wire diameter and an end, and positioning a conductor at a distance from the end of the wire. The method further includes creating an electrical discharge between the conductor and the end, while setting the distance and an electrical potential of the discharge, so as to create a bead of a predefined size on the end. The method also includes assembling the wire with the created bead into an invasive probe, so that the bead is positioned at an outer surface of the probe.

14 Claims, 6 Drawing Sheets

(51) Int. Cl.
*A61N 1/05* (2006.01)
*A61B 5/00* (2006.01)
*A61B 18/08* (2006.01)
*A61B 5/25* (2021.01)
*A61B 5/283* (2021.01)
*A61B 5/291* (2021.01)
*A61B 5/339* (2021.01)
*A61B 18/00* (2006.01)

(52) U.S. Cl.
CPC .............. *A61B 5/339* (2021.01); *A61B 5/6852* (2013.01); *A61B 18/082* (2013.01); *A61B 18/1492* (2013.01); *A61N 1/0529* (2013.01); *A61N 1/0565* (2013.01); *A61B 18/14* (2013.01); *A61B 2018/00017* (2013.01); *A61B 2018/00083* (2013.01); *A61B 2018/00351* (2013.01); *A61B 2018/00577* (2013.01); *A61B 2018/00964* (2013.01); *A61B 2018/1417* (2013.01); *A61B 2018/1467* (2013.01); *A61B 2218/002* (2013.01); *A61B 2562/0209* (2013.01); *A61B 2562/125* (2013.01); *Y10T 29/49174* (2015.01)

(58) Field of Classification Search
CPC .............. A61B 18/1492; A61B 18/14; A61B 2018/00017; A61B 2018/00083; A61B 2018/00351; A61B 2018/00577; A61B 2018/00964; A61B 2018/1417; A61B 2018/1467; A61B 2218/002; A61B 2562/0209; A61B 2562/125; A61N 1/0529; A61N 1/0565; Y10T 29/49174
See application file for complete search history.

(56) References Cited

U.S. PATENT DOCUMENTS

| | | | |
|---|---|---|---|
| 5,286,944 A | | 2/1994 | Li |
| 5,579,764 A | * | 12/1996 | Goldreyer ............... A61N 1/06 600/512 |
| 5,893,884 A | | 4/1999 | Tu |
| 6,898,848 B2 | | 5/2005 | Ohkubo et al. |
| 6,898,849 B2 | * | 5/2005 | Trejo ...................... H01L 24/78 228/179.1 |
| 2001/0007070 A1 | * | 7/2001 | Stewart ............... A61B 18/1492 606/41 |
| 2002/0087208 A1 | * | 7/2002 | Koblish ............. A61B 18/1492 606/41 |
| 2004/0019350 A1 | * | 1/2004 | O'Brien ............. A61B 18/1442 606/49 |
| 2004/0243121 A1 | * | 12/2004 | Lee .................... A61B 18/1492 606/41 |
| 2005/0267460 A1 | * | 12/2005 | Roop ................. A61B 18/1492 606/41 |
| 2009/0209950 A1 | * | 8/2009 | Starksen ........... A61B 18/1492 606/41 |
| 2011/0130816 A1 | * | 6/2011 | Howard ................. H01R 43/00 607/116 |
| 2013/0060245 A1 | | 3/2013 | Grunewald et al. |
| 2013/0123775 A1 | * | 5/2013 | Grunewald ........ A61B 18/1492 606/41 |
| 2014/0047712 A1 | | 2/2014 | Evans et al. |

FOREIGN PATENT DOCUMENTS

| | | |
|---|---|---|
| JP | 2000-223067 | 8/2000 |
| JP | 2000 235995 | 8/2000 |
| JP | 2009-112794 | 5/2009 |

OTHER PUBLICATIONS

CNIPA First Office Action dated Jun. 30, 2020, in corresponding CN Application No. 201610908229.4, English translation, 9 pages.
CNIPA Search Report dated Jun. 22, 2020, for corresponding CN Application No. 201610908229.4, English translation, 2 pages.
JPO Notification of Reasons for Refusal dated Sep. 29, 2020, for corresponding JP Patent Application No. 2016-204153, English translation, 3 pages.
EPO Examination Report dated Mar. 26, 2018, issued in corresponding EP Patent Application No. 16 194 402.0, 5 pages.

* cited by examiner

PREPARATION OF MICRO-ELECTRODES

CROSS REFERENCE TO RELATED APPLICATIONS

This application is a divisional application of U.S. patent application Ser. No. 14/886,761, filed Oct. 19, 2015, the entire contents of which is hereby incorporated by reference.

FIELD OF THE INVENTION

The present invention relates generally to electrode preparation, and specifically to preparation of extremely small electrodes.

BACKGROUND OF THE INVENTION

Invasive medical probes or catheters used for cardiac procedures typically use electrodes in order to acquire potentials of a region of the heart being investigated or being operated on. The electrodes may also be used to inject current into the heart, for example for ablation, pacing, or for determining a location of the probe. In order to minimize trauma to the patient involved, the probe typically has a diameter that is as small as possible, The small size of the probes consequently means that the electrodes of the probes have a correspondingly extremely small size. Furthermore, in some cases it is desirable that one probe should have a number of electrodes that are spatially separated and electrically insulated from each other. Such multiple electrode probes can be used for simultaneous potential acquisition from, and/or simultaneous ablation of, spatially separated sites in the heart. However, the multiple electrodes of necessity have to be of an extremely small size.

Other types of procedures using electrodes, such as electroencephalographic procedures, also benefit from using small probes with extremely small electrodes, so as to minimize trauma to patients.

U. S. Patent Application 2013/0060245, to Grunewald et al., whose disclosure is incorporated herein by reference, describes an ablation catheter adapted for direct tissue contact. The catheter is stated to have micro-elements that provide more accurate sensing of tissue, including thermal and electrical properties for temperature and impedance measurements. The micro-elements extend through a hollow chamber of an irrigated ablation electrode, and distal ends of the micro-elements can protrude outside of the electrode or be flush with the electrode.

Japanese Patent Publication JP2000-235995, to Kyomasu Ryuichi, whose disclosure is incorporated herein by reference, describes a ball forming method for wire bonding. The disclosure states that a high voltage is applied between the tip of a wire extending from the bottom of a capillary and a discharge electrode, forming a ball at the tip of the wire.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a method, including:

providing a metal wire having a wire diameter and an end;

positioning a conductor at a distance from the end of the wire;

creating an electrical discharge between the conductor and the end, while setting the distance and an electrical potential of the discharge, so as to create a bead of a predefined size on the end; and assembling the wire with the created bead into an invasive probe, so that the bead is positioned at an outer surface of the probe.

Typically, the metal wire has another end, and the method includes attaching a further metal wire to the other end to make an electrical contact, and assembling the wire includes assembling the wire with the created bead and the attached further metal wire into the invasive probe. The method may further include sliding then shrinking shrink sleeving over the created bead, the metal wire, the electrical contact, and the further metal wire.

In a disclosed embodiment the method includes sliding an electrically insulating sleeve over a portion of the wire not including the bead. Typically, the method includes sliding the sleeve to butt against the bead. The method may also include assembling the wire with the created bead and the electrically insulating sleeve into the invasive probe.

In a further disclosed embodiment the conductor includes a further wire, and the distance includes the distance from an end of the further wire to the end of the metal wire. Typically, the further wire and the metal wire are aligned collinearly.

In a yet further disclosed embodiment the distance is 0.1 mm or less.

In an alternative embodiment, the bead has a spherical bead-surface. The spherical bead-surface may be flush with the outer surface of the probe. Alternatively, the spherical bead-surface protrudes from the outer surface of the probe by a radius of the spherical bead-surface. The method may include polishing the spherical bead-surface to be flush with the outer surface of the probe. Further alternatively, the spherical bead-surface is recessed into the outer surface of the probe by a radius of the spherical bead-surface.

In a further alternative embodiment the method includes providing natural air cooling to the conductor and the end during the electrical discharge.

There is further provided, according to an embodiment of the present invention, apparatus, including:

a metal wire having a wire diameter and an end;

a conductor, positioned at a distance from the end of the wire;

a bead of a predefined size formed on the end by creating an electrical discharge between the conductor and the end, while setting the distance and an electrical potential of the discharge; and an invasive probe configured to receive the wire with the created bead, so that the bead is positioned at an outer surface of the probe.

The present disclosure will be more fully understood from the following detailed description of the embodiments thereof, taken together with the drawings, in which:

DETAILED DESCRIPTION OF EMBODIMENTS

Overview

Micro-electrodes on the distal end of an invasive probe typically have an extremely small diameter, in some cases of about 400 microns. The micro-electrodes are typically of an inert metal such as platinum, gold, palladium, iridium, or an alloy formed from these metals, and to form the micro-electrodes a prior art system attaches, by soldering, an extremely small platinum bead to a conducting wire that is already in the distal end. The attachment can be tedious and time consuming, as well as requiring specialized equipment that can manipulate and solder extremely small entities.

Embodiments of the present invention overcome these problems. A first end of a short metal wire, typically made of an inert metal such as platinum, is positioned at a distance from a conductor. The conductor is typically also in the form of a wire, and is herein also termed a "spark" wire. An electrical discharge, or spark, is created between the spark wire and the first end of the inert metal wire, while setting the distance and an electrical potential of the discharge, between the spark wire and the first end, so as to create a bead of a predefined size on the first end of the inert metal wire.

Once the bead has been created, the inert wire with its bead is assembled into an invasive probe, so that the bead is positioned at an outer surface of the probe.

Typically, prior to creation of the bead, the second end of the short metal wire is attached to a conducting wire, typically of copper. An electrically insulating plastic sleeve, such as a polyimide sleeve, may be slid over the combination, after which the bead may be formed on the first end of the short metal wire as described above. The sleeved combination, with its created bead, may then be inserted into an aperture of the probe, a diameter of the aperture being set to correspond with an external diameter of the sleeve. The insertion typically causes the sleeve to butt against the bead so that after insertion the bead, which acts as a micro-electrode, is insulated from the probe, and so that the sleeved combination acts to seal the aperture.

In embodiments of the present invention a bead of a given size may be easily produced by setting specific values for the distance and electrical potential referred to above. Furthermore, the method of production of the bead eliminates the necessity of soldering the bead, as is required in prior art methods of micro-electrode assembly.

System Description

Figure 1:
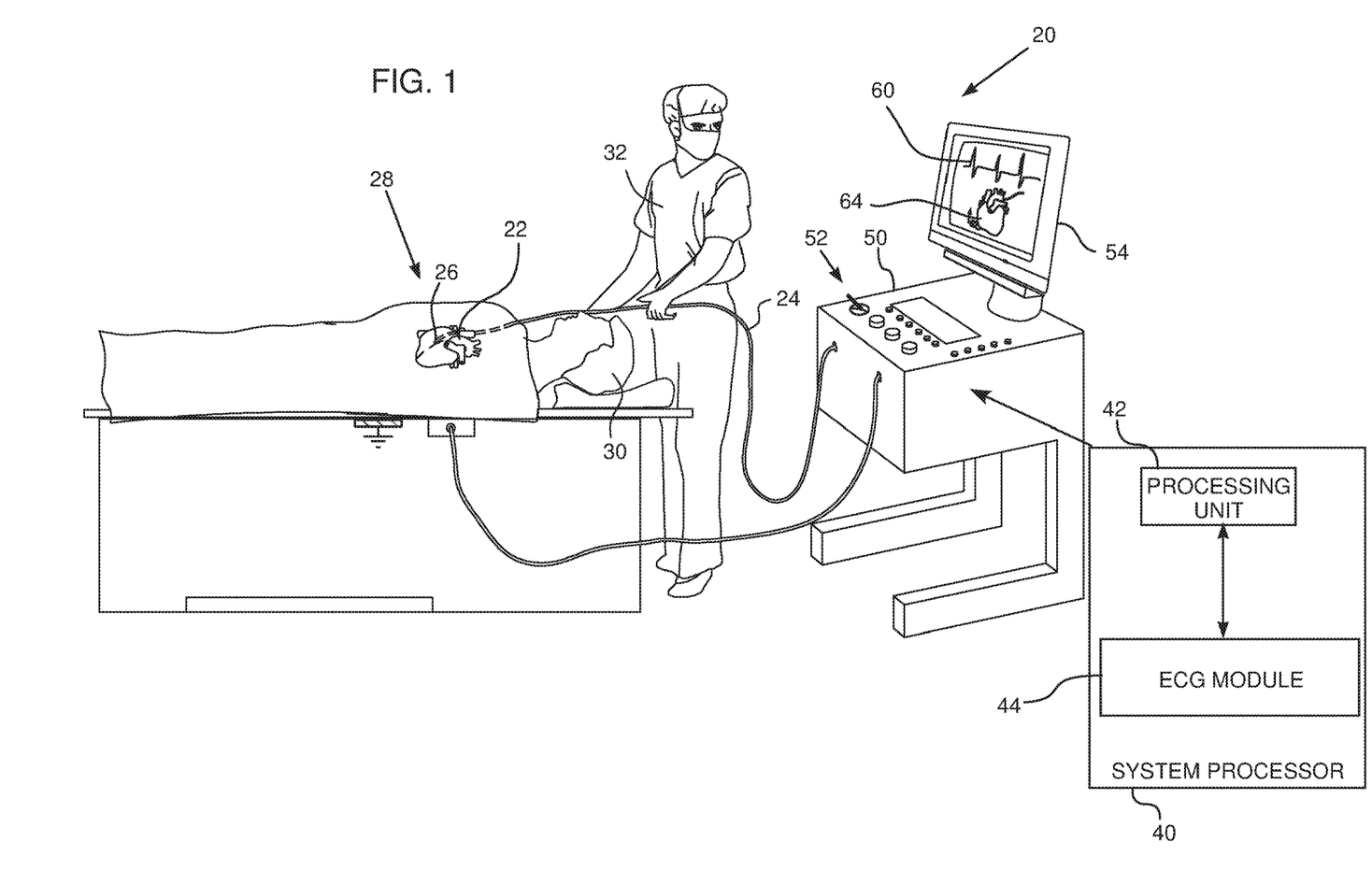
FIG. 1 is a schematic illustration of a catheterization system, according to an embodiment of the present invention.

Reference is now made to FIG. 1, which is a schematic illustration of a catheterization system 20, according to an embodiment of the present invention. System 20 is typically used during a medical procedure on a body organ, the procedure, inter alia, being assumed to acquire electrical signals from the organ, and/or to inject electrical signals to the organ. In the description herein the body organ, by way of example, is assumed to comprise the heart, wherein the system is applied to acquire intra-cardiac electrocardiogram (ECG) signals from the heart. However, it will be understood that system 20 may be applied to acquire and/or inject substantially any electrical signals from/to any body organ, such as acquiring electroencephalograph (EEG) signals from the brain.

The following description assumes that system 20 senses intra-cardiac ECG signals from a heart 22, using a probe 24. A distal end 26 of the probe is assumed to have at least one micro-electrode assembly 28 for sensing the signals. The structure and formation of assembly 28 is described in more detail below, as is the incorporation of the assembly into distal end 26. Typically, probe 24 comprises a catheter which is inserted into the body of a subject 30 during a cardiac procedure performed by a user 32 of system 20. In the description herein user 32 is assumed to be a medical professional.

System 20 may be controlled by a system processor 40, comprising a processing unit 42 communicating with an ECG module 44. Processor 40 may be mounted in a console 50, which comprises operating controls 52 that typically include a pointing device such as a mouse or trackball. Professional 32 uses the operating controls to interact with the processor, which, as described below, may be used to present results produced by system 20 to the professional on a screen 54.

The screen displays results of analysis and processing of ECG signals acquired by one or more electrodes within assembly 28, after the signals have been transferred to ECG module 44. Typically, the resultant ECG signals are presented on screen 54 in the form of a potential vs. time graph, and a schematic example 60 of such a graph is illustrated in FIG. 1. However, the resultant ECG signals, obtained from the ECG module, may also be used by processor 40 to derive other results associated with the ECG signals, such as a local activation time (LAT). These results are typically presented on screen 54 in the form of a three-dimensional (3D) map 64 of the internal surface of heart 22.

Processor 40 uses software stored in a memory of the processor to operate system 20. The software may be downloaded to processor 40 in electronic form, over a network, for example, or it may, alternatively or additionally, be provided and/or stored on non-transitory tangible media, such as magnetic, optical, or electronic memory.

Processor 40 typically comprises other modules apart from ECG module 44, such as a probe tracking module, a force module that measures a force on distal end 26, an irrigation module controlling irrigation fluid for the distal end, and an ablation module that provides regulated power to the distal end. For simplicity, such modules are not shown in FIG. 1. The Carto® system produced by Biosense Webster, of Diamond Bar, CA, uses an ECG module such as ECG module 44, as well as the other modules referred to herein.

Figure 2:
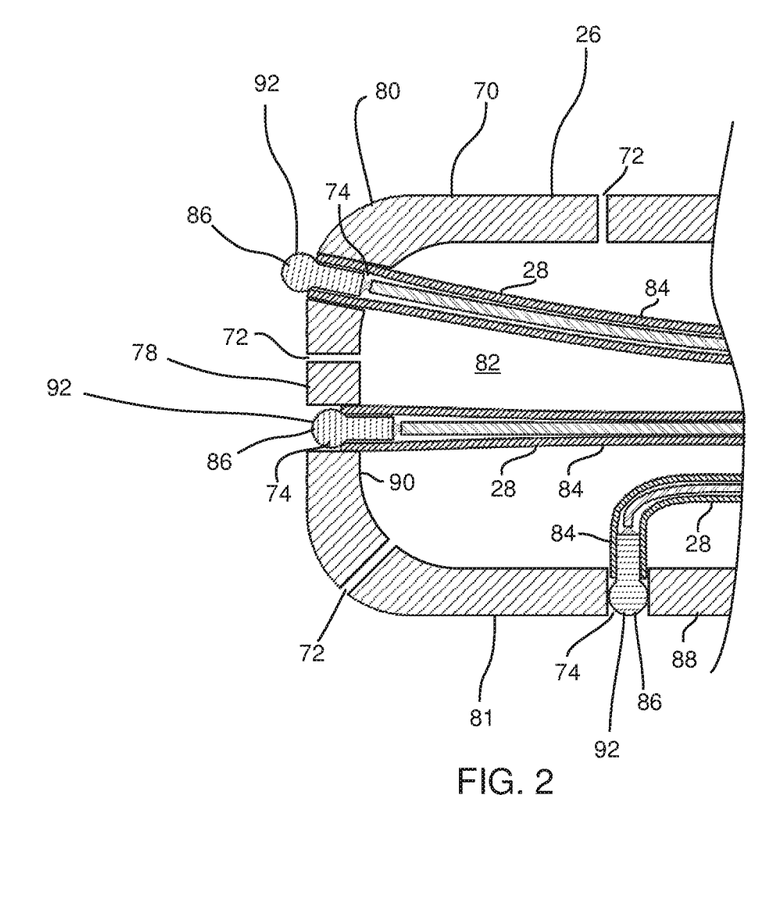
FIG. 2 is a schematic diagram illustrating a portion of a distal end of a probe in cross-section, according to an embodiment of the present invention.

FIG. 2 is a schematic diagram illustrating a portion of distal end 26 in cross-section, according to an embodiment of the present invention. Distal end 26 is assumed, by way of example, to be formed of a conductive dome 70, into which irrigation apertures 72 and assembly apertures 74 have been formed. By way of example, three irrigation apertures 72 are shown in FIG. 2, but typically there are many more than three such apertures, and the irrigation apertures may be formed in substantially any part of dome 70. Also by way of example, three assembly apertures 74 are shown in FIG. 2, but there may be as few as one, or two or more such apertures formed in the dome, and the assembly apertures may be formed in substantially any part of the dome, including, as is illustrated, a plane end 78 of the dome, an edge 80 of the plane end, and a wall of the dome.

Dome 70 may be generally similar in structure to the dome described in U.S. Patent Application 2013/0060245 referenced above.

Dome 70 has an outer surface 88 and an inner surface 90, the latter forming an outer surface of a cavity 82 enclosed by the dome. Cavity 82 may be configured to receive irrigation fluid that is expelled via apertures 72. As is explained below, assemblies 28 are inserted into respected assembly apertures 74 so that respective proximal portions 84 of the assemblies enter and traverse cavity 82, while respective distal portions 86 of the assemblies are at outer surface 88 of dome 70.

After insertion a micro-electrode 92 in distal portion 86 may protrude slightly from outer surface 88, as exemplified in FIG. 2 for assembly 28 in assembly aperture of edge 80. Alternatively, after insertion micro-electrode 92 in distal portion 86 may be recessed slightly with respect to outer surface 88, as exemplified in the figure for assembly 28 in assembly aperture 74 of end 78. Further alternatively, after insertion the micro-electrode in distal portion 86 may be approximately flush with outer surface 88, as exemplified in the figure for assembly 28 in assembly aperture 74 of wall 81. In some embodiments a secondary polishing step may be performed to contour the bead so that it exactly matches the exterior surface geometry.

Regardless of whether micro-electrode 92 protrudes from, is flush with, or is recessed into surface 88, after insertion of a given assembly 28 within its respective aperture the micro-electrode is able to receive and transmit electrical signals from tissue when dome 70 contacts the tissue.

The formation of micro-electrode 92 is described below.

Figures 3A, 3B:
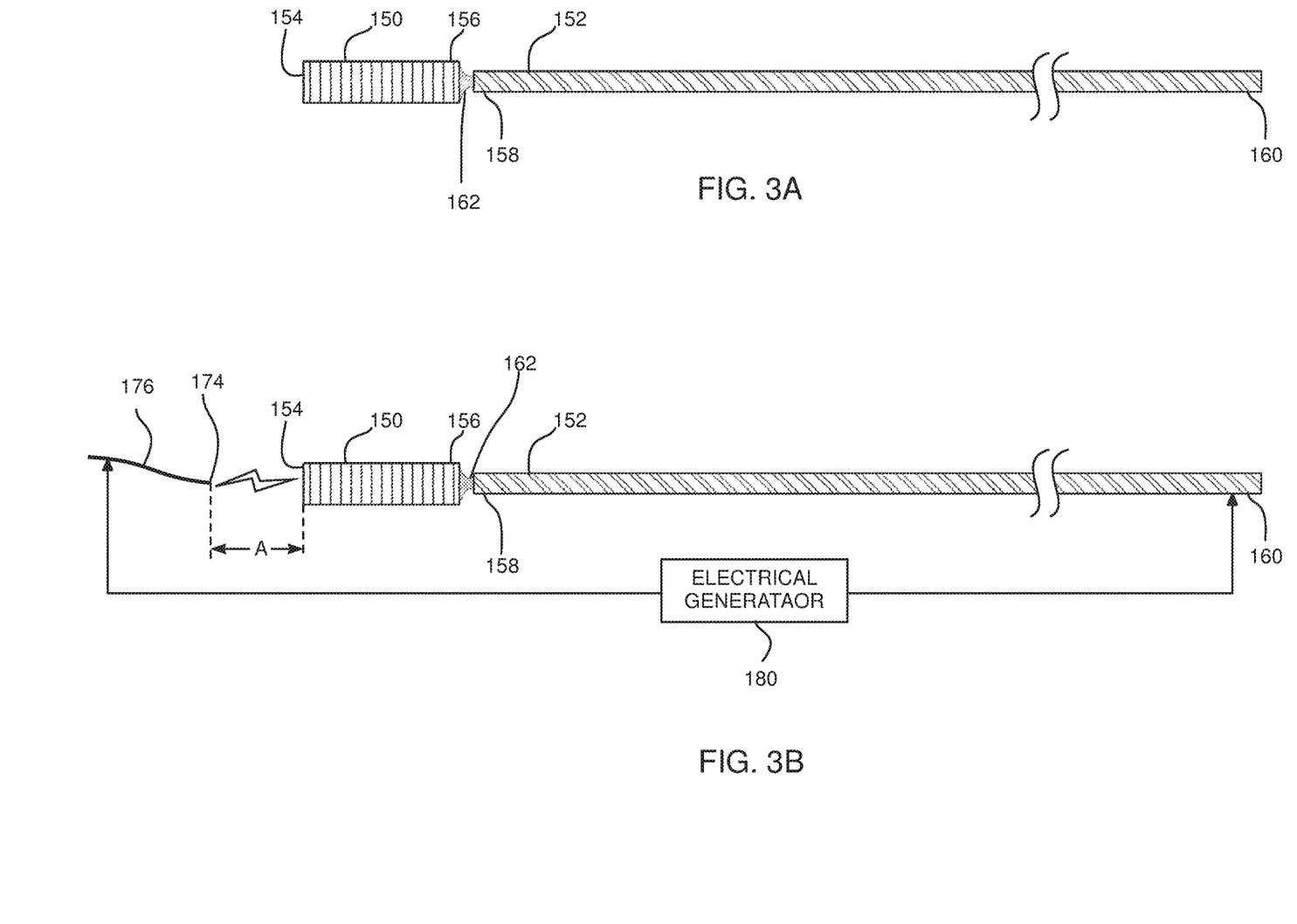
FIGS. 3A-3F illustrate stages in the formation of a micro-electrode assembly, according to an embodiment of the present invention.
Figure 3C:
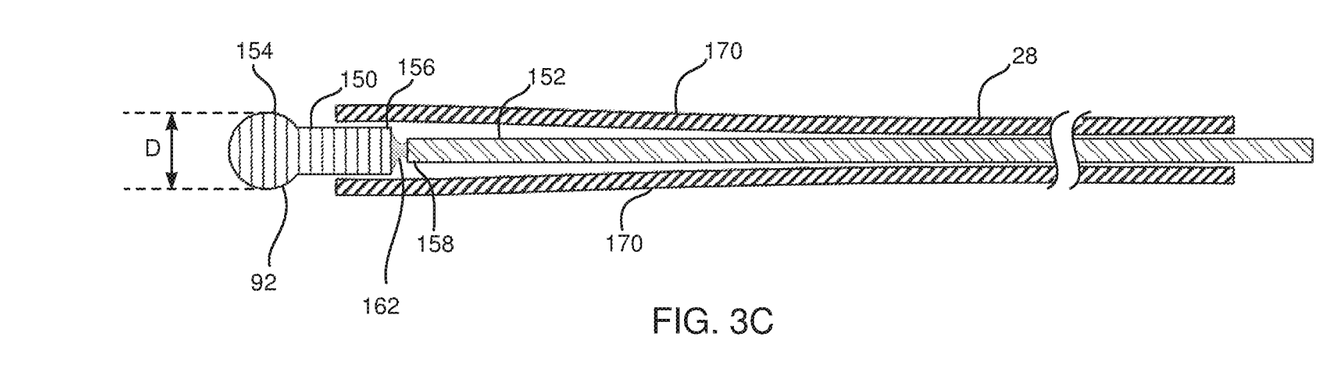
Figure 3D:
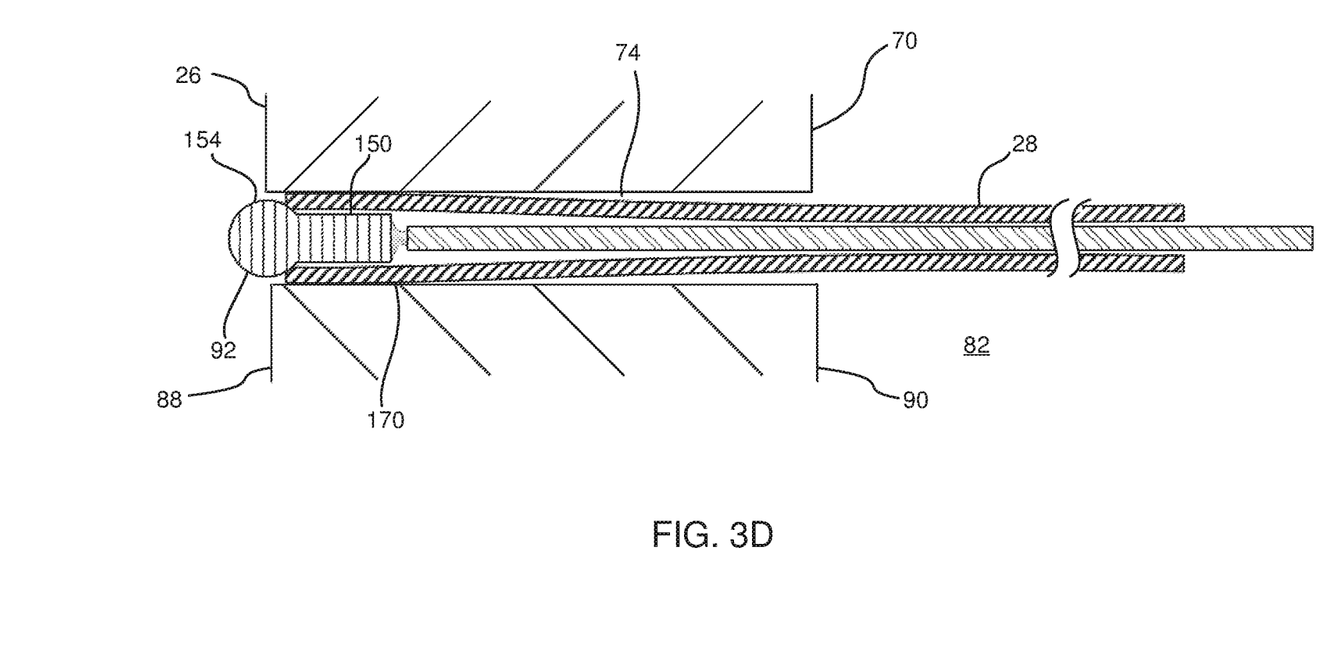
Figure 3E:
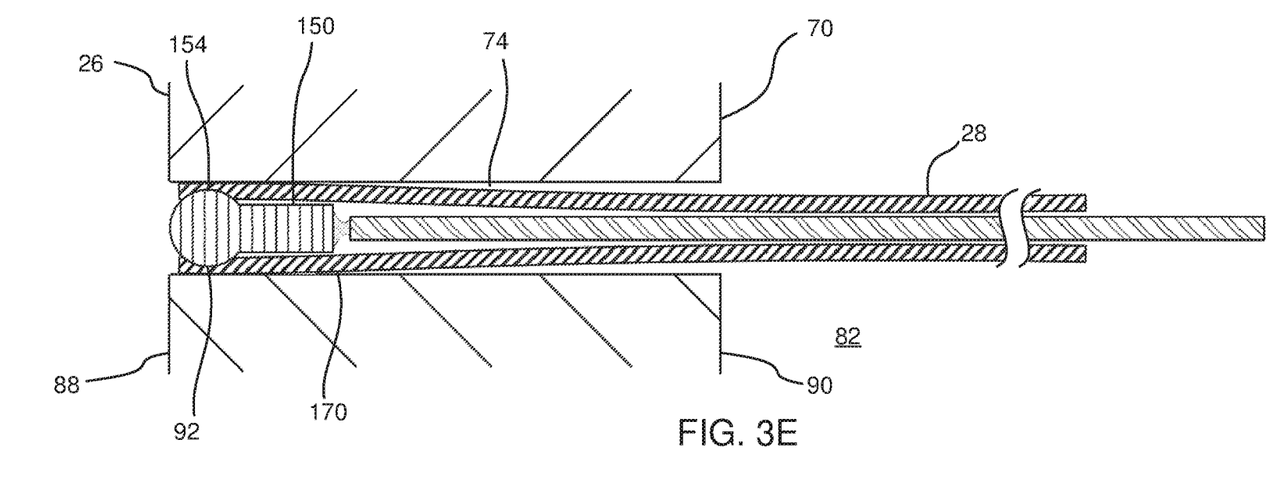
Figure 3F:
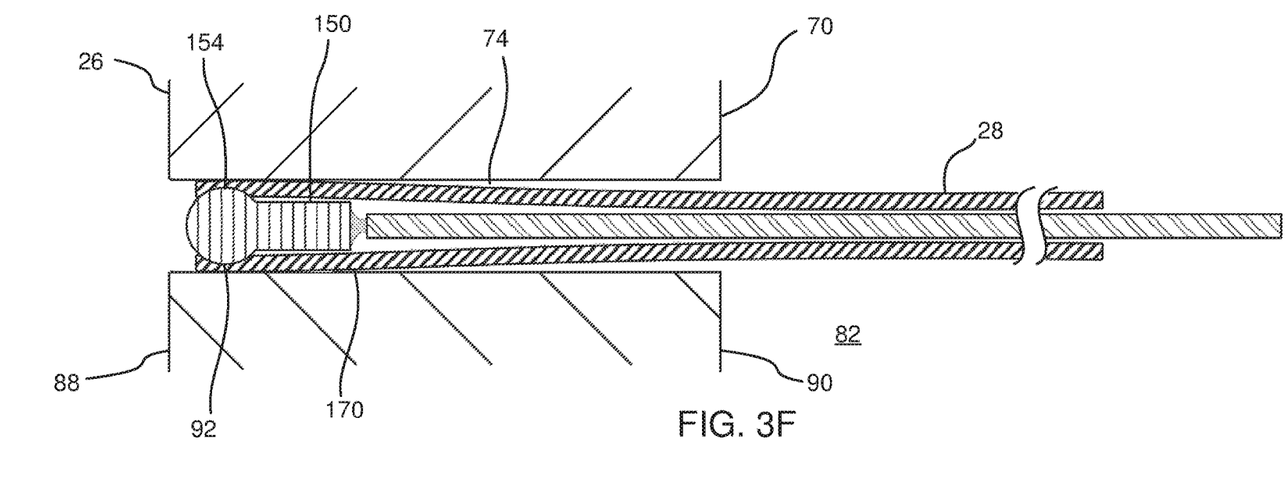
Figure 4:
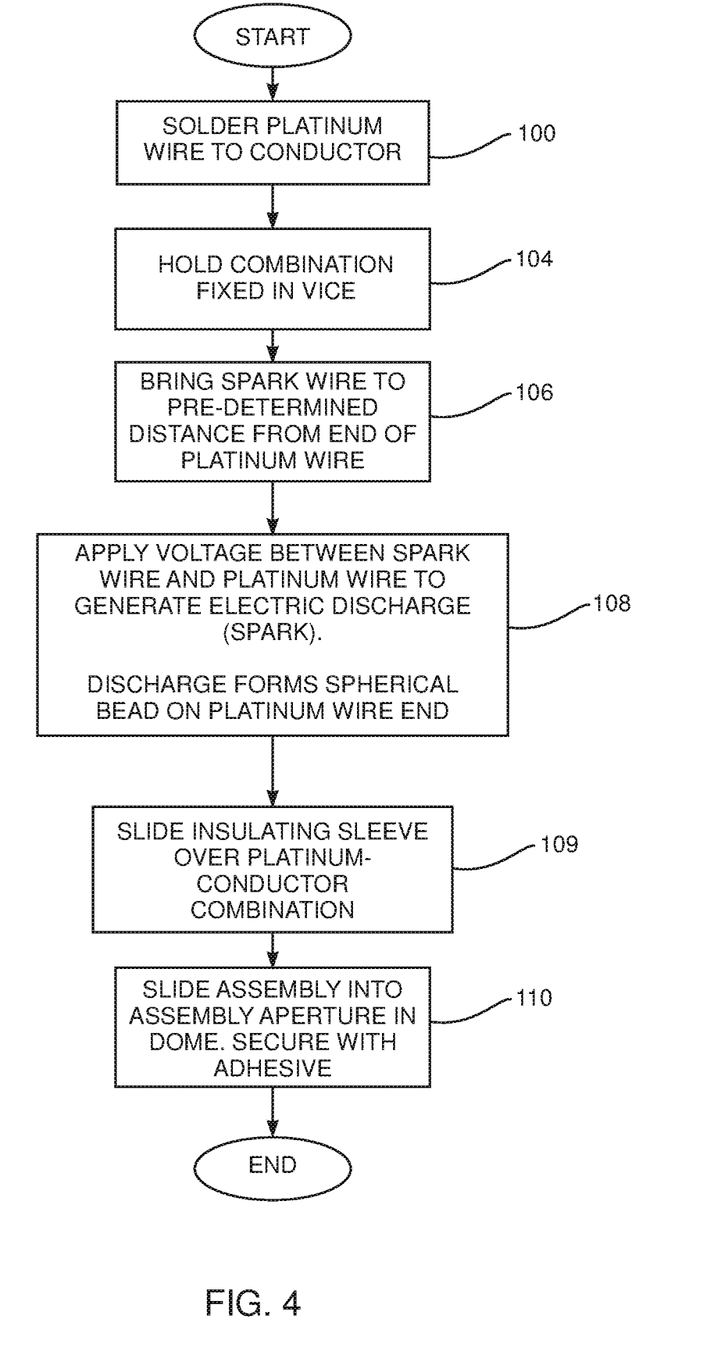
FIG. 4 is a flowchart of steps in the formation of and incorporation of the assembly into the distal end of the probe, according to an embodiment of the present invention.

FIGS. 3A-3F illustrate stages in the formation of assembly 28, and FIG. 4 is a flowchart of steps in the formation of the assembly and incorporation of the assembly into distal end 26, according to an embodiment of the present invention. In an initial step 100, a metallic biocompatible inert conductive wire 150, herein assumed to comprise platinum, is attached, typically by soldering, resistance welding, or laser welding, to another conductor 152 in the form of a wire, typically copper. Inert metal wire 150 has a distal end 154 and a proximal end 156. Conductor 152 has a distal end 158 and a proximal end 160. The process of attachment connects proximal end 156 of the inert wire to distal end 158 of the conductor by a joint 162 so that the two conductors are fixedly held together. Step 100 is illustrated schematically in FIG. 3A, and in an embodiment of the present invention, inert wire 150 has an approximate length of 3 mm and an approximate diameter of 175 microns. Typically, although not necessarily, conductor 152 has a diameter smaller than the diameter of inert conductive wire 150.

In a first preparatory step 104, the combination formed in step 102 is mounted in a fixed position, typically by being gripped in a vice.

In a second preparatory step 106, a pointed tip 174 of a conductor 176, typically a conductive wire, is positioned a measured distance "A" from inert wire distal end 154. In some embodiments distance "A" is approximately 0.1 mm or less. Typically, the two wires should be collinear, but may be in any convenient orientation, for example horizontal or vertical. Conductor 176 is also referred to herein as spark wire 176. An electrical generator 180 is connected between spark wire 176 and conductor 152. In some embodiments generator 180 comprises a resistance welder, such as a Miyachi Unitek model UB29 resistance welder produced by Amada Miyachi of Monrovia, CA, which provides a high DC current.

In an electrode formation step 108, a voltage level of generator 180 is adjusted so that when activated, the generator forms an electric discharge, in air, also herein referred to as a spark, between tip 174 and inert wire distal end 154. The generator is activated, typically at a voltage of approximately 1 V and for a duration of approximately 5 ms, during which approximately 200 A of DC current flows, so as to cause the electric discharge. The discharge deforms distal end 154 into micro-electrode 92, which is in the form of a bead that is typically partly spherical in shape and that remains attached to inert wire 150. In one embodiment, the spark was generated with the generator set to provide at least 100 amps for between 1 and 10 ms.

The spark is formed extremely quickly, and the inventors have found that natural air cooling, rather than forced air cooling, is sufficient for formation of the micro-electrode. Micro-electrode 92 is also referred to herein as bead 92. Formation of bead 92 concludes the process of forming assembly 28, prior to its insertion into distal end 26 of probe 24.

FIG. 3B schematically illustrates steps 102-108 up to the formation of bead 92, and FIG. 3C schematically illustrates completed micro-electrode assembly 28 after formation of bead 92. Bead 92 has a diameter D, which is greater than the diameter of inert wire 150. In some embodiments diameter D is approximately 400 microns.

In a sleeve application step 109, an insulating sleeve 170, typically of a plastic such as a polyimide, is slid over the inert wire-conductor combination formed in step 100. An initial internal diameter of sleeve 170 in an unexpanded form is configured to be slightly less than the diameter of inert wire 150. The operation of sliding is implemented so that sleeve 170 expands and grips inert wire 150, i.e., so that the internal diameter of the sleeve in its expanded form, at the region of inert wire 150, equals the diameter of the inert wire.

The operation of sliding is also implemented so that sleeve 170 covers joint 162, but so that micro-electrode 92 is uncovered by the sleeve.

Alternatively, thin-wall shrink sleeving can be used over the combination. By applying a shrinking process to the sleeving, the sleeving conforms to the bead, the inert wire, and the conductive wire, serving to electrically isolate the combination.

In a final fabrication step 110, completed micro-electrode assembly 28, produced in step 109, is slid into a selected assembly aperture 74 in dome 70. The aperture is configured to have a diameter that accommodates the diameter of the insulating sleeve, but not that of the bead. After the microassembly is seated in the selected assembly aperture, it is then secured using adhesive.

The incorporation of any given assembly 28 into a respective assembly aperture 74 concludes with bead 92 slightly protruding from outer surface 88, being approximately flush with the surface, or being slightly recessed into the surface.

FIGS. 3D, 3E, and 3F schematically illustrate step 110, after assembly 28 has been inserted into aperture 74, so that bead 92 respectively protrudes from outer surface 88, is approximately flush with the surface, and is slightly recessed into the surface. A typical protrusion distance is the radius of the bead, so that a 400 micron bead may protrude by 200 microns from the surface. A typical recess distance is approximately the same as the typical protrusion distance.

If required, any protrusion of the micro-electrode can be eliminated by polishing the surface of dome 70, e.g., by buffing, after the assembly has been secured with adhesive.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:
1. An apparatus comprising:
   (a) a metal wire comprising:
      (i) a proximal end defining a wire diameter, and
      (ii) a distal end that includes a solderless spherical bead defining a spherical bead surface and a bead diameter that is greater than the wire diameter; and
   (b) a conductor wire with a proximal end that is directly coupled with the proximal end of the metal wire at a joint, the joint being soldered or welded;
   (c) an invasive probe that includes a distal end, the distal end of the invasive probe comprising:
      (i) an electrically conductive dome with a wall comprising a circumferential portion and an end portion and defining a cavity therein;
      (ii) an inner surface,
      (iii) an outer surface,
      (iv) at least one irrigation aperture at one location in the dome, and
      (v) at least one assembly aperture at another location in the dome extending between the inner and outer surfaces, wherein the solderless spherical bead is positioned at least partially within the assembly aperture and fixedly sealed therein with adhesive in one of three positions of (i) the spherical bead surface protruding past the outer surface of the distal end of the invasive probe by a radius of the spherical bead; (ii) the spherical bead surface being flush with the outer surface, or (iii) the spherical bead surface being recessed from the outer surface by the radius of the spherical bead; and
   (d) an elongated electrically-insulative expandable sleeve with a distal end within the assembly aperture, generally proximal of the solderless spherical bead, and circumferentially surrounding the proximal end of the metal wire and at least a distal portion of the conductor wire extending through the cavity.

2. The apparatus according to claim 1, wherein the sleeve comprises a shrink sleeving that is slid then shrunk over the metal wire, the joint, and the conductor wire.

3. The apparatus according to claim 1, wherein the electrically insulating sleeve is butted against the solderless spherical bead.

4. The apparatus according to claim 1, wherein the solderless spherical bead is formed from the metal wire on the distal end by creating an electrical discharge between a spark wire and the distal end, while setting a distance and an electrical potential of the electrical discharge.

5. The apparatus according to claim 1, wherein the metal wire is integrally formed together as a unitary piece.

6. The apparatus according to claim 1, wherein the conductor wire has a diameter that is smaller than the wire diameter.

7. The apparatus according to claim 1, wherein the metal wire has a length of approximately 3 millimeters.

8. The apparatus according to claim 1, wherein the assembly aperture defines a diameter that accommodates the insulating sleeve but not both insulating sleeve and the solderless bead.

9. The apparatus according to claim 1, wherein the sleeve is configured with an internal unexpanded diameter, an internal expanded diameter and an outer expanded diameter, wherein:
   the internal unexpanded diameter is slightly smaller than the wire diameter of the metal wire;
   the internal expanded diameter is equal to the wire diameter; and
   the external expanded diameter is configured for insertion into the assembly aperture but greater than the spherical bead.

10. An apparatus comprising:
    (a) an inert metal wire comprising:
       (i) a proximal end defining a wire diameter of approximately 175 microns; and
       (ii) a distal end that includes a solderless spherical bead defining a bead diameter of approximately 400 microns; and
    (b) a conductor wire directly coupled with the proximal end of the metal wire at a joint that is soldered or welded, the conductor wire having a diameter lesser than the wire diameter; and
    (c) an invasive probe that includes an electrically-conductive distal end, the distal end of the invasive probe comprising a shell with:
       (i) an inner surface,
       (ii) an outer surface, and
       (iii) at least one aperture extending between the inner and outer surfaces, wherein the solderless spherical bead is positioned at least partially within the aperture.

11. The apparatus of claim 10, wherein the inert metal wire includes a platinum wire.

12. The apparatus of claim 10, wherein the conductor wire includes a copper wire.

13. An apparatus comprising:
    (a) a metal wire comprising:
       (i) a proximal end defining a wire diameter, and
       (ii) a distal end that includes a solderless spherical bead defining a spherical bead surface and a bead diameter that is greater than the wire diameter; and
    (b) a conductor wire with a proximal end that is directly coupled with the proximal end of the metal wire at a joint, the joint being soldered or welded and
    (c) an invasive probe that includes a distal end, the distal end of the invasive probe comprising:
       (i) an electrically conductive dome with a wall comprising a circumferential portion and an end portion and defining a cavity therein;
       (ii) an inner surface,
       (iii) an outer surface,
       (iv) at least one irrigation aperture at one location in the dome, and
       (v) at least one assembly aperture at another location in the dome extending between the inner and outer surfaces, wherein the solderless spherical bead is positioned at least partially within the assembly aperture and fixedly sealed therein with adhesive in one of three positions of (i) the spherical bead surface protruding past the outer surface of the distal end of the invasive probe by a radius of the spherical bead; (ii) the spherical bead surface being flush with the outer surface, or (iii) the spherical bead surface being recessed from the outer surface by the radius of the spherical bead.

14. The apparatus according to claim 13, wherein the solderless bead is formed from the metal wire on the distal end by creating an electrical discharge between a spark wire and the distal end, while setting a distance and an electrical potential of the electrical discharge.

\* \* \* \* \*